(12) United States Patent
Ushida et al.

(10) Patent No.: US 12,311,130 B2
(45) Date of Patent: May 27, 2025

(54) GUIDE WIRE

(71) Applicant: ASAHI INTECC CO., LTD., Seto (JP)

(72) Inventors: Keisuke Ushida, Seto (JP); Kenji Yoshida, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 962 days.

(21) Appl. No.: 17/126,402

(22) Filed: Dec. 18, 2020

(65) Prior Publication Data

US 2021/0128886 A1 May 6, 2021

Related U.S. Application Data

(63) Continuation of application No. PCT/JP2018/024857, filed on Jun. 29, 2018.

(51) Int. Cl.
*A61M 25/09* (2006.01)

(52) U.S. Cl.
CPC ... *A61M 25/09* (2013.01); *A61M 2025/09091* (2013.01); *A61M 2025/09133* (2013.01); *A61M 2205/0216* (2013.01)

(58) Field of Classification Search
CPC ........ A61M 25/09; A61M 2025/09091; A61M 2025/09133; A61M 2205/0216; A61M 25/09016; A61M 2025/09141; A61M 2025/0915; A61M 2025/09175

See application file for complete search history.

(56) References Cited

U.S. PATENT DOCUMENTS

| 6,001,068 A | 12/1999 | Uchino et al. |
| 6,602,208 B2 | 8/2003 | Jafari |
| 7,758,520 B2 * | 7/2010 | Griffin .................. A61M 25/09 600/585 |
| 2004/0039308 A1 | 2/2004 | Murayama et al. |
| 2008/0045908 A1 | 2/2008 | Gould et al. |
| 2008/0171217 A1 | 7/2008 | Mishima |
| 2008/0183182 A1 | 7/2008 | Satou et al. |
| 2008/0281396 A1 * | 11/2008 | Ishida .................. A61L 31/022 623/1.11 |

(Continued)

FOREIGN PATENT DOCUMENTS

| JP | H04-292174 A | 10/1992 |
| JP | H11-57014 A | 3/1999 |

(Continued)

OTHER PUBLICATIONS

U.S. Appl. No. 17/119,583, filed Dec. 11, 2020 in the name of Ushida et al.

*Primary Examiner* — Alex M Valvis
*Assistant Examiner* — Jonathan M Haney
(74) *Attorney, Agent, or Firm* — Oliff PLC

(57) ABSTRACT

A guide wire including a first core shaft made of a superelastic material, and a second core shaft made of a material more susceptible to plastic deformation than of the first core shaft and joined to a distal end side of the first core shaft on a proximal end side. On a joint part between the first core shaft and the second core shaft, the first core shaft and the second core shaft are adjacent to each other in a first direction. A flat portion where a length in the first direction in a transverse section is longer than a length in a second direction orthogonal to the first direction is formed on a distal end portion of the second core shaft.

15 Claims, 16 Drawing Sheets

(56) References Cited

U.S. PATENT DOCUMENTS

| | | | |
|---|---|---|---|
| 2009/0254000 A1* | 10/2009 | Layman | A61M 25/01 600/585 |
| 2010/0274085 A1* | 10/2010 | Mugan | A61M 25/10184 600/115 |
| 2011/0015618 A1 | 1/2011 | Satou et al. | |
| 2011/0160703 A1 | 6/2011 | Matsumoto et al. | |
| 2013/0226033 A1* | 8/2013 | Eskuri | A61M 25/09 600/585 |
| 2015/0005746 A1 | 1/2015 | Sato | |
| 2015/0119757 A1* | 4/2015 | Sato | D07B 1/12 600/585 |
| 2017/0072170 A1 | 3/2017 | Akitomo | |
| 2019/0262588 A1* | 8/2019 | Kambara | A61M 25/09 |

FOREIGN PATENT DOCUMENTS

| | | |
|---|---|---|
| JP | 2003-260140 A | 9/2003 |
| JP | 2004-016359 A | 1/2004 |
| JP | 2006-508739 A | 3/2006 |
| JP | 2006-511304 A | 4/2006 |
| JP | 2006-519069 A | 8/2006 |
| JP | 2007-503957 A | 3/2007 |
| JP | 2008-161589 A | 7/2008 |
| JP | 2008-188670 A | 8/2008 |
| JP | 4203358 B2 | 12/2008 |
| JP | 2010-503484 A | 2/2010 |
| JP | 2010-240201 A | 10/2010 |
| JP | 2011-130976 A | 7/2011 |
| JP | 2013-544575 A | 12/2013 |
| JP | 2016-189998 A | 11/2016 |
| JP | 2017-080153 A | 5/2017 |
| JP | 2017-513604 A | 6/2017 |
| JP | 2017-521177 A | 8/2017 |
| NO | 95/19800 A2 | 7/1995 |
| WO | 1998/018516 A1 | 5/1998 |
| WO | 2004/050162 A1 | 6/2004 |
| WO | 2004/060462 A2 | 7/2004 |
| WO | 2004/075967 A1 | 9/2004 |
| WO | 2005/023357 A2 | 3/2005 |
| WO | 2008/034010 A2 | 3/2008 |
| WO | 2008/139829 A1 | 11/2008 |
| WO | 2009/119386 A1 | 10/2009 |
| WO | 2009/119387 A1 | 10/2009 |
| WO | 2012/058302 A1 | 5/2012 |
| WO | 2013/136581 A1 | 9/2013 |
| WO | 2015/164250 A1 | 10/2015 |
| WO | 2016/012902 A1 | 1/2016 |
| WO | 2016/047555 A1 | 3/2016 |

\* cited by examiner

GUIDE WIRE

CROSS REFERENCE TO RELATED APPLICATION

This is a Continuation of PCT/JP2018/024857 filed Jun. 29, 2018. The disclosure of the prior application is hereby incorporated by reference herein in its entirety.

TECHNICAL FIELD

The disclosed embodiments relate to a guide wire.

BACKGROUND

A guide wire used for inserting a catheter or the like into a blood vessel is known. In such a guide wire, a small curve, or the like is formed on a distal end portion of the guide wire for the purpose of improving blood vessel selectivity to smoothly lead the guide wire to a target site in a blood vessel in some cases. For example, Patent Literatures 1 to 3 disclose a guide wire in which shaping of a distal end portion is facilitated by joining (connecting) a shaping ribbon (second long flexible member, ribbon) made of stainless steel to a distal end of a wire main body (first long flexible member, long shaft) made of a nickel-titanium alloy.

Herein, the wire main body is joined to the shaping ribbon by applying soldering or brazing between the wire main body and the shaping ribbon adjacent to each other. Thus, on the joint part between the wire main body and the shaping ribbon, the guide wire tends to curve perpendicular to an adjacent direction between the wire main body and the shaping ribbon (direction in parallel with each other). On the other hand, on the distal end side of the joint part, the guide wire freely curves in any direction. As a result, the guide wires described in Patent Literatures 1 to 3 have had a problem that, when the distal end side is shaped, torsion is caused between the joint part and the distal end side of the joint part, and therefore the guide wire tends to have a three-dimensional shape.

Incidentally, such problems are not limited to vascular systems, and are common to guide wires to be inserted into each organ in a human body, such as a lymphatic system, a biliary system, a urinary system, a respiratory system, a digestive system, a secretory gland, and a genital organ. In addition, such a problem is not limited to the guide wire including the shaft made of a nickel-titanium alloy and the shaft made of stainless steel, and is common to guide wires formed by joining a plurality of core shafts.

CITATION LIST

Patent Literature

Patent Literature 1: WO2009/119386, brochure
Patent Literature 2: Japanese Unexamined Patent Application Publication (Translation of PCT Application) No. 2017-521177
Patent Literature 3: Japanese Unexamined Patent Application Publication (Translation of PCT Application) No. 2006-519069

SUMMARY

The disclosed embodiments are directed to solving the aforementioned problems, and an object of the disclosed embodiments is to facilitate shaping of the distal end portion and to prevent torsion of the shaped portion, in the guide wire.

The disclosed embodiments include the following aspects.

(1) According to an aspect of the disclosed embodiments, a guide wire is provided. The guide wire includes a first core shaft made of a superelastic material, and a second core shaft made of a material more susceptible to plastic deformation than of the first core shaft and joined to a distal end side of the first core shaft on a proximal end side. On a joint part between the first core shaft and the second core shaft, the first core shaft and the second core shaft are adjacent to each other in a first direction. A flat portion where a length in the first direction in a transverse section is longer than a length in a second direction orthogonal to the first direction is formed on a distal end portion of the second core shaft.

According to this configuration, since the second core shaft made of the material more susceptible to plastic deformation than of the first core shaft is joined to the distal end side of the first core shaft made of the superelastic material, a distal end portion of the guide wire can be easily shaped. In addition, on the flat portion formed on the distal end portion of the second core shaft, the length in the first direction in which the first and second core shafts are adjacent to each other is longer than the length in the second direction orthogonal to the first direction. Thus, similarly to the joint part, on the flat portion, the second core shaft tends to curve perpendicular to the adjacent direction (first direction) between the first and second core shafts (tents to curve in the second direction). In such a way, the curvable directions are conformed to each other between the joint part and the distal end side of the joint part, so that the shaped portion can be prevented from being distorted in the guide wire having this configuration.

(2) In the guide wire according to the aforementioned aspect, the second core shaft further includes a large-diameter portion where the length in the first direction and the length in the second direction are substantially equal in the transverse section, and an intermediate portion disposed between the large-diameter portion and the flat portion. The joint part may be disposed on the large-diameter portion. According to this configuration, in the large-diameter portion formed on a proximal end side of the second core shaft, the length in the first direction and the length in the second direction are substantially conformed to each other, so that breakage of the second core shaft accompanying the shaping can be prevented. In addition, in the flat portion formed on the distal end side of the second core shaft, torsion of the second core shaft accompanying the shaping can be prevented as described above.

(3) The guide wire according to the aforementioned aspect may be configured such that the length in the first direction of the flat portion is longer than the length in the first direction of the large-diameter portion, and the length in the second direction of the flat portion is shorter than the length in the second direction of the large-diameter portion. According to this configuration, in the second core shaft, the length in the first direction of the flat portion is longer than the length in the first direction of the large-diameter portion, and the length in the second direction of the flat portion is shorter than the length in the second direction of the large-diameter portion. Thus, the flat portion can be easily formed e.g. by pressing a distal end side of a cylindrical member or a quadrangular prism-shaped member in which a length in the first direction and a length in the second direction are substantially equal.

(4) The guide wire according to the above aspect further includes a covering portion for covering the joint part between the first core shaft and the second core shaft, and at least a part on the distal end side of the joint part in the second core shaft. From the distal end side to the proximal end side of the guide wire, a first region where the second core shaft on the distal end side of the joint part is covered by the covering portion, and a second region adjacent to the first region, where the joint part is covered by the covering portion, are disposed. The first region may be more susceptible to plastic deformation than the second region. According to this configuration, the distal end side of the guide wire has the first region more susceptible to plastic deformation than the second region adjacent to the proximal end side of the first region, and therefore the distal end portion of the guide wire can be easily shaped. In addition, the covering portion for covering the joint part between the first and second core shafts, and at least a part of the second core shaft on the distal end side of the joint part is disposed on both the first and second regions. Owing to this covering portion, a rigidity gap between the first and second core shafts having different rigidities can be reduced, and therefore the joint part between the first and second core shafts can be easily shaped. Furthermore, a part locally susceptible to deformation in the vicinity of the joint part, or the like is protected to prevent breakage of the first and second core shafts, so that durability of the guide wire can be improved.

(5) In the guide wire according to the aforementioned aspect, a transverse sectional shape of the first core shaft on the joint part may be different from a transverse sectional shape of the second core shaft on the joint part. According to this configuration, since the transverse sectional shape of the first core shaft and the transverse sectional shape of the second core shaft are different from each other on the joint part between the first and second core shafts, a contact face of the first and second core shafts increases between the first and second core shaft adjacent to each other on the joint part, compared to a case of the same shapes. With the guide wire configured in this manner, the joining strength of the first and second core shafts can be improved by filling this contact face as a joining face with a joining agent.

(6) The guide wire according to the aforementioned aspect may be configured such that a decreasing-diameter portion where an outer diameter of the first core shaft decreases from the proximal end side to the distal end side is formed on the distal end side of the first core shaft, and the joint part is disposed on the decreasing-diameter portion. According to this configuration, when the decreasing-diameter portion having the decreasing outer diameter is formed on the distal end side of the first core shaft and the second core shaft is joined to this decreasing-diameter portion (a joint part is formed), the joint part includes a large-diameter portion of the first core shaft, so that durability of the guide wire can be improved.

Incidentally, the disclosed embodiments can be achieved in various aspects, e.g. in a form of a core shaft product composed of a plurality of core shafts used in a guide wire, a method for manufacturing a guide wire, or the like.

DETAILED DESCRIPTION

First Embodiment

Figure 1:
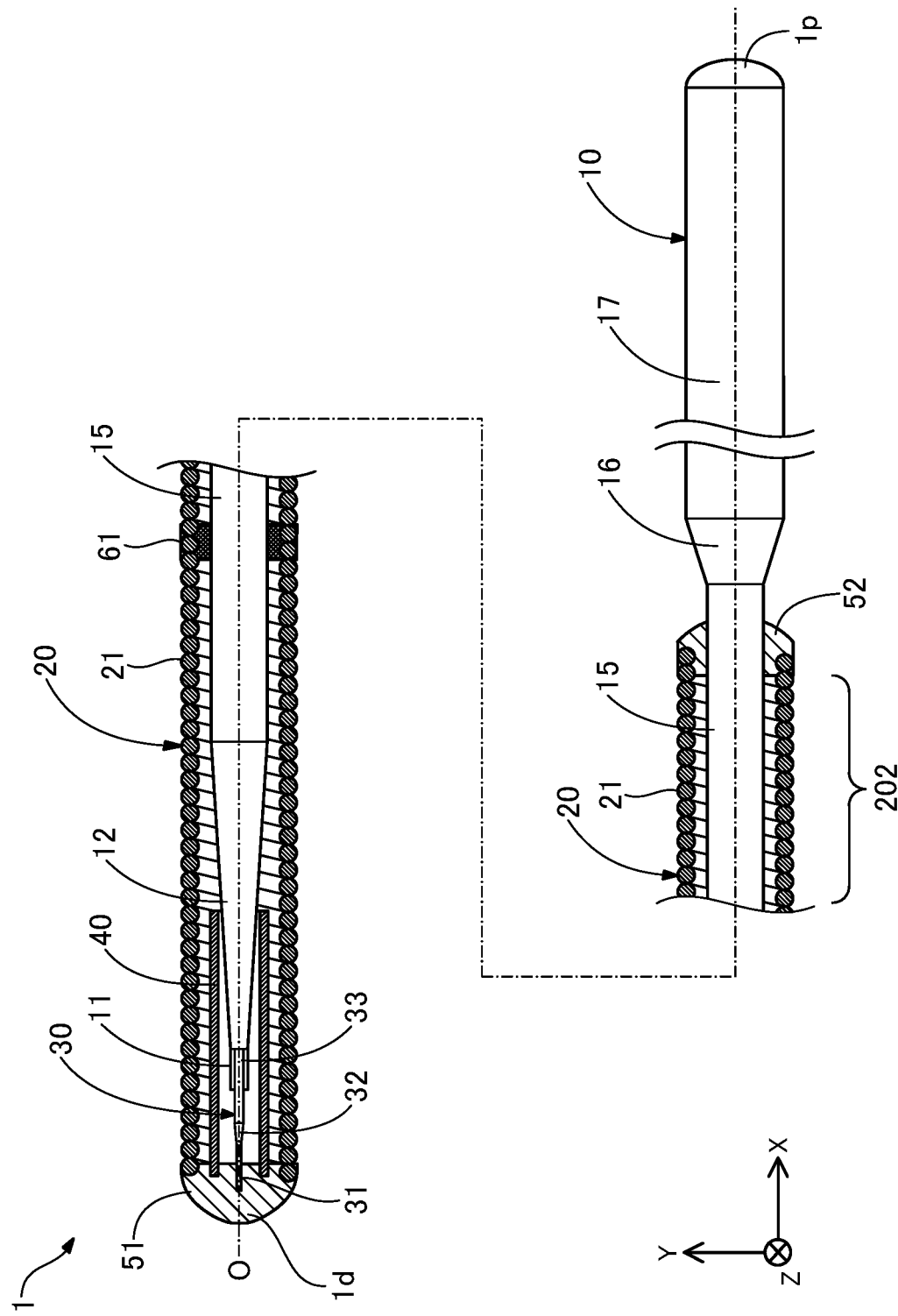
FIG. 1 is a partial sectional view illustrating an overall configuration of a guide wire according to the first embodiment.

FIG. 1 is a partial sectional view illustrating an overall configuration of a guide wire 1 according to the first embodiment. The guide wire 1 is e.g. a medical appliance used for inserting a catheter into a blood vessel, and includes a first core shaft 10, a coil body 20, a second core shaft 30, a covering portion 40, a distal end-side fixation portion 51, a proximal end-side fixation portion 52, and an intermediate fixation portion 61. In FIG. 1, an axis passing through a center of the guide wire 1 is represented by an axis line O (dot and dash line). In the following examples, all of an axis passing through a center of the first core shaft 10 on a proximal end side of a first large-diameter portion 15, an axis passing through a center of the coil body 20, and an axis passing through a center of the covering portion 40 coincide with the axis line O. However, each of the axis passing through the center of the first core shaft 10, the axis passing through the center of the coil body 20, and the axis passing through the center of the covering portion 40 may be inconsistent with the axis line O.

In addition, XYZ axes that are orthogonal to each other are illustrated in FIG. 1. The X axis corresponds to the axis direction of the guide wire 1, the Y axis corresponds to a height direction of the guide wire 1, and the Z axis corresponds to a width direction of the guide wire 1. The left side (−X axis direction) of FIG. 1 is referred to as "distal end side" of the guide wire 1 and each component, and the right side of FIG. 1 (+X axis direction) is referred to as "proximal end side" of guide wire 1 and each component. In addition, regarding the guide wire 1 and each component, the end portion positioned on the distal end side is referred to as "distal end portion" or simply "distal end", the end portion positioned on the proximal end side is referred to as "proximal end portion" or simply "proximal end". In the first embodiment, the distal end side corresponds to "farther side", and the proximal end side corresponds to "nearer side". These features are common to the figures illustrating the overall configuration in FIG. 1 and the other figures.

The first core shaft 10 is a long, tapered member with a large diameter on the proximal end side and a small diameter on the distal end side. The first core shaft 10 is made of a superelastic material e.g. a NiTi (nickel-titanium) alloy, or an alloy of NiTi and another metal. The first core shaft 10 has a small-diameter portion 11, a first decreasing-diameter portion 12, a first large-diameter portion 15, a second decreasing-diameter portion 16, a second large-diameter portion 17, in this order from the distal end side to the proximal end side. An outer diameter and a length of each portion can be arbitrarily determined.

Figure 2:
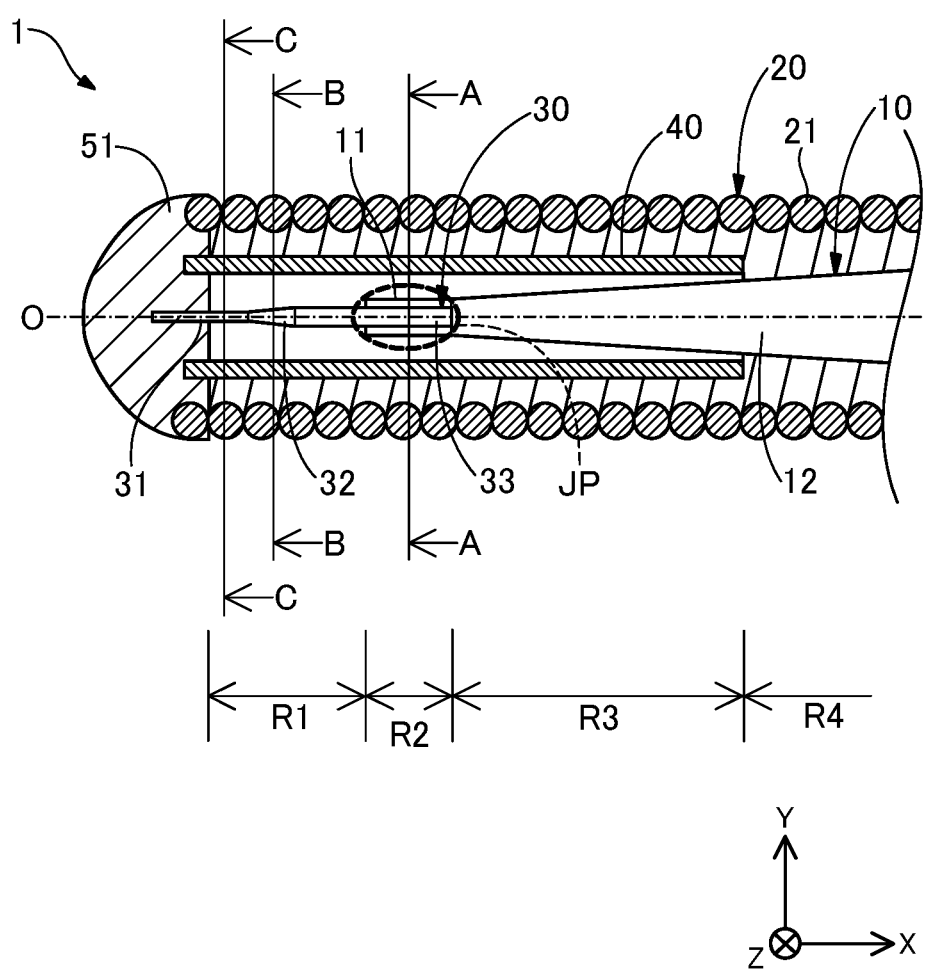
FIG. 2 is a partial sectional view illustrating a distal end side of the guide wire.
Figure 3:
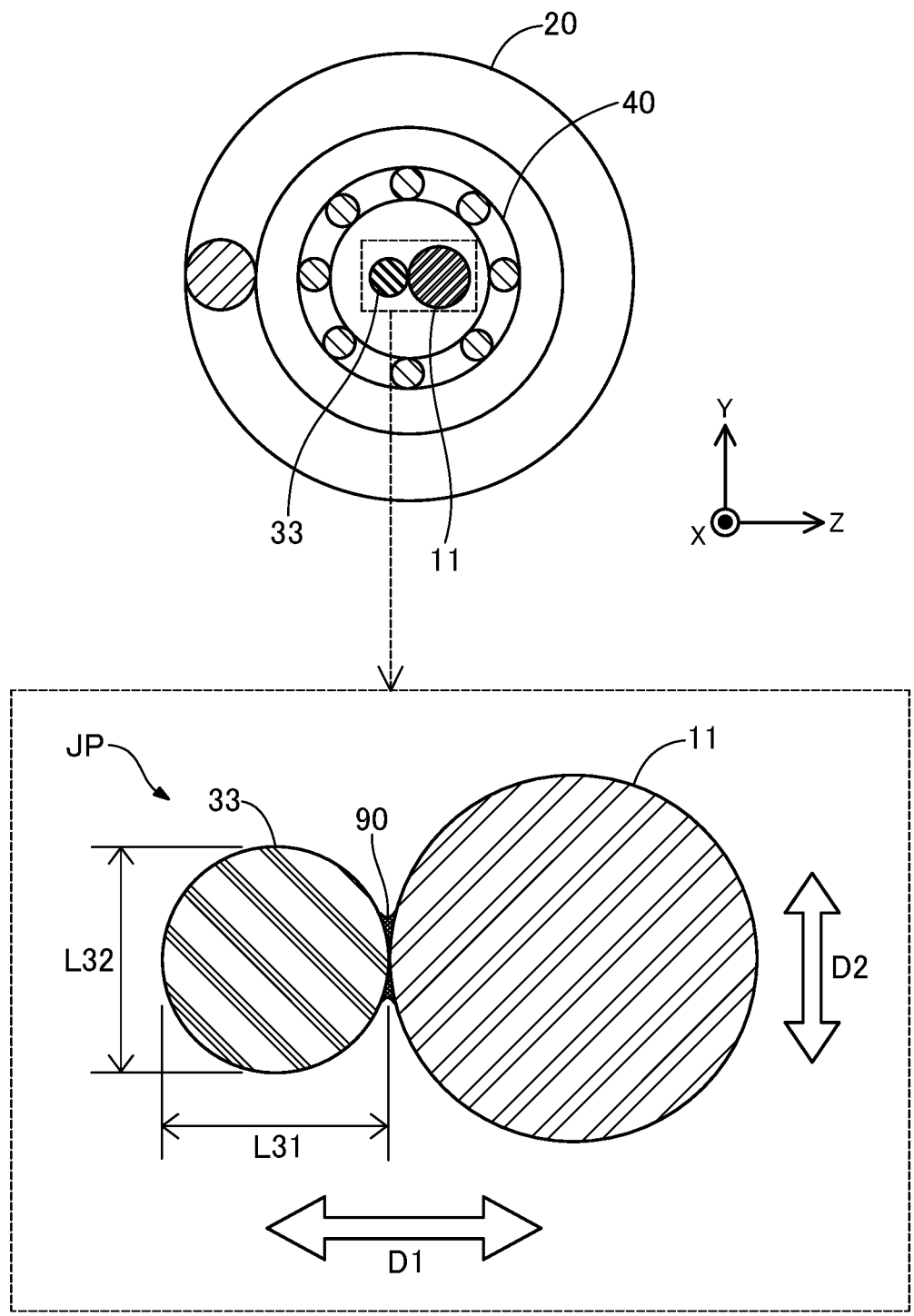
FIG. 3 is a sectional view illustrating the guide wire taken along line A-A (FIG. 2).

FIG. 2 is a partial sectional view illustrating the distal end side of the guide wire 1. FIG. 3 is a sectional view illustrating the guide wire 1 taken along line A-A (FIG. 2). In FIG. 3, the sectional view taken along line A-A is illustrated in an upper column, and a partial enlarged view of the vicinity of the joint part JP is illustrated in a lower column. The XYZ axes illustrated in FIG. 2 and FIG. 3 correspond to the XYZ axes respectively in FIG. 1. The same applies to the figures with XYZ axes in FIG. 3 and the following figures.

The small-diameter portion 11 of the first core shaft 10 is disposed on the distal end side of the first core shaft 10. The small-diameter portion 11 is a portion where the outer diameter of the first core shaft 10 is the smallest, and has a substantially circular transverse sectional shape as illustrated in FIG. 3. In FIG. 3, the transverse sectional shape of the small-diameter portion 11 is illustrated as a circle having the substantially equal lengths in the Y-axis direction and the Z-axis direction. Incidentally, the transverse sectional shape of the small-diameter portion 11 may be arbitrarily determined, and may be e.g. a substantially rectangle such as a substantially square and a substantially rectangle, or a substantially ellipse. When the transverse sectional shape is a substantially rectangle, the corners may be R-chamfered or C-chamfered.

The first decreasing-diameter portion 12 is disposed between the small-diameter portion 11 and the first large-diameter portion 15. The first decreasing-diameter portion 12 has a substantially truncated cone shape with an outer diameter reducing from the proximal end side to the distal end side. The first large-diameter portion 15 is disposed between the first decreasing-diameter portion 12 and the second decreasing-diameter portion 16. The first large-diameter portion 15 has a substantially cylindrical shape with a certain outer diameter larger than an outer diameter of the small-diameter portion 11. The second decreasing-diameter portion 16 is disposed between the first large-diameter portion 15 and the second large-diameter portion 17. The second decreasing-diameter portion 16 has a substantially truncated cone shape with an outer diameter reducing from the proximal end side to the distal end side. The second large-diameter portion 17 is disposed on the proximal end side of the first core shaft 10. The second large-diameter portion 17 has a substantially cylindrical shape having a certain outer diameter equivalent to the largest outer diameter of the first core shaft 10.

The outer side faces of the small-diameter portion 11, the first decreasing-diameter portion 12, and the first large-diameter portion 15 are covered by the coil body 20 described later. On the other hand, the second decreasing-diameter portion 16 and the second large-diameter portion 17 are not covered by the coil body 20 but are exposed from the coil body 20. The second large-diameter portion 17 is used when an operator grasps the guide wire 1.

The coil body 20 has a substantially cylindrical shape formed by spirally winding a wire 21 around the first core shaft 10 and the second core shaft 30. The wire 21 forming the coil body 20 may be a solid wire composed of one wire, or a twisted wire obtained by twisting a plurality of wires. When the wire 21 is a solid wire, the coil body 20 is configured as a single coil, and when the wire 21 is the twisted wire, the coil body 20 is configured as a hollow twisted wire coil. Alternatively, the coil body 20 may be configured by combining the single coil and the hollow twisted wire coil. The wire diameter of the wire 21 and an average coil diameter in the coil body 20 (average diameter of the outer diameter and the inner diameter of the coil body 20) can be arbitrarily determined.

The wire 21 can be made of, for example, a stainless steel alloy such as SUS304 and SUS316, a superelastic alloy such as a NiTi alloy, a piano wire, a radiolucent alloy such as nickel-chromium alloy and cobalt alloy, gold, platinum, tungsten, or a radiopaque alloy such as an alloy including the aforementioned elements (e.g. platinum-nickel alloy). Incidentally, the wire 21 may be made of a known material other than the aforementioned materials.

The second core shaft 30 is a long member extending from the proximal end side to the distal end side, and has a flat portion 31, an intermediate portion 32, and a large-diameter portion 33. The second core shaft 30 is made of a material more susceptible to plastic deformation than of the first core shaft 10, e.g. a stainless steel alloy such as SUS304 and SUS316. The second core shaft 30 is also referred to as "ribbon". As illustrated in FIG. 2, the large-diameter portion positioned on the proximal end side of the second core shaft 30 is joined to the small-diameter portion 11 positioned on the distal end side of the first core shaft 10. This joining can be performed in such a way that a gap between the first core shaft 10 (small-diameter portion 11) and the second core shaft 30 (large-diameter portion 33) adjacent to each other is filled with a joining agent 90 and the joining agent 90 is hardened as illustrated in the lower column of FIG. 3. As the joining agent 90, e.g. a metal solder such as silver solder, gold solder, zinc, Sn—Ag alloy, and Au—Sn alloy, or an adhesive such as epoxy adhesive can be used.

In FIG. 2 and FIG. 3, the joint part between the first core shaft 10 and the second core shaft 30 is referred to as "joint part JP". In addition, on the joint part JP, the direction in which the first core shaft 10 and the second core shaft 30 are adjacent to each other is referred to as "first direction D1", and the direction orthogonal to the first direction D1 (direction perpendicular to the first direction D1) is referred to as "second direction D2" (lower column of FIG. 3, white arrow). In the embodiment of the figure, the first direction D1 corresponds to the Z-axis direction, and the second direction D2 corresponds to the Y-axis direction.

Figure 4:
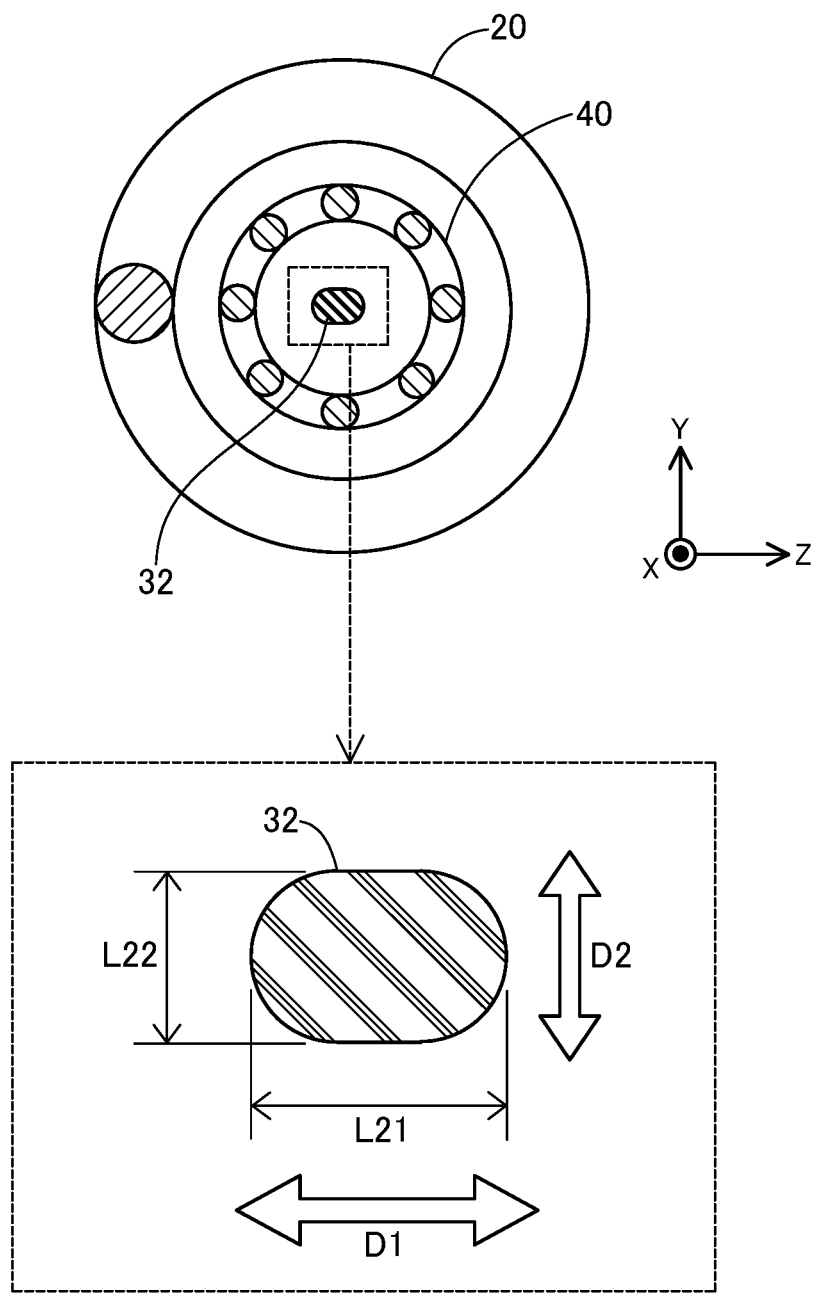
FIG. 4 is a sectional view illustrating the guide wire taken along line B-B (FIG. 2).
Figure 5:
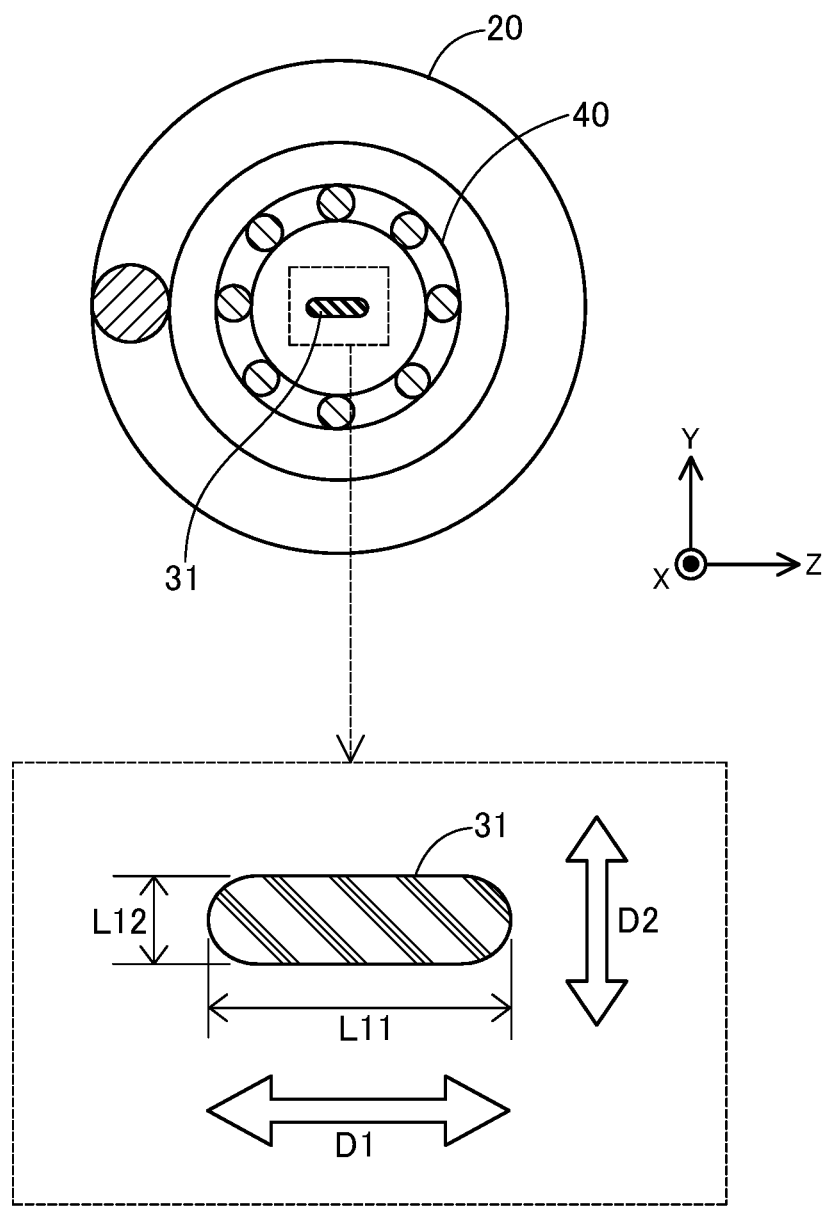
FIG. 5 is a sectional view illustrating the guide wire taken along line C-C (FIG. 2).

FIG. 4 is a sectional view illustrating the guide wire 1 taken along line B-B (FIG. 2). FIG. 5 is a sectional view illustrating the guide wire 1 taken along line C-C (FIG. 2). In FIG. 4 and FIG. 5, sectional views taken along line B-B and line C-C are illustrated in the upper columns, and partial enlarged views of the second core shaft 30 are illustrated in the lower columns. The large-diameter portion 33 of the second core shaft 30 is disposed on the proximal end side of the second core shaft 30. As illustrated in the lower column of FIG. 3, the large-diameter portion 33 has a substantially circular transverse sectional shape in which a length L31 in the first direction D1 and a length L32 in the second direction D2 are substantially equal. The intermediate portion 32 of the second core shaft 30 is disposed between the large-diameter portion 33 and the flat portion 31. As illustrated in the lower column of FIG. 4, the intermediate portion 32 has a substantially elliptical transverse sectional shape in which a length L21 in the first direction D1 is longer than a length L22 in the second direction D2. The flat portion 31 of the second core shaft 30 is disposed on the distal end side of the second core shaft 30. As illustrated in the lower column of FIG. 5, the flat portion 31 has a substantially flat transverse sectional shape in which a length L11 in the first direction D1 is longer than a length L12 in the second direction D2.

Figure 6:
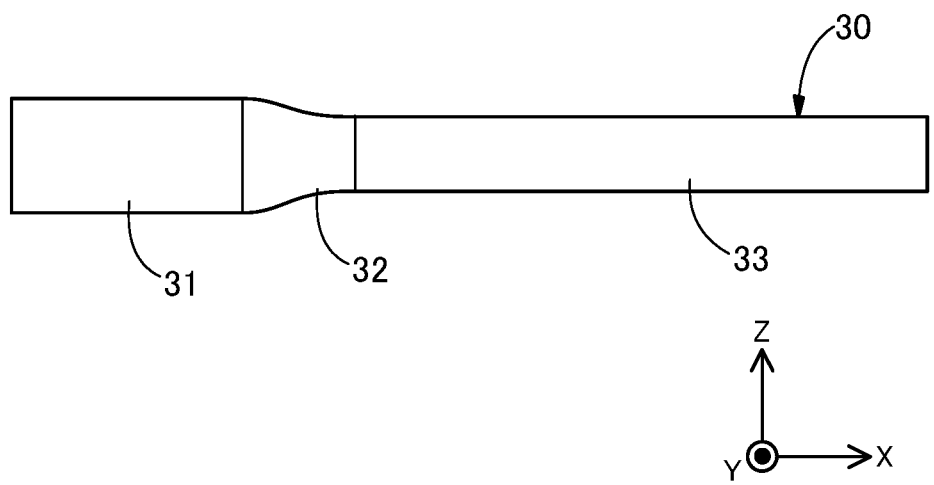
FIG. 6 is a diagram illustrating an appearance of a second core shaft viewed from a Y-axis direction.

FIG. 6 is a diagram illustrating an appearance of the second core shaft 30 viewed from a Y-axis direction. In the second core shaft 30, the length of each portion in the first direction D1 gradually decreases from the flat portion 31 to the large-diameter portion 33 in "descending order of L11, L21, and L31". Additionally, in the second core shaft 30, the length of each portion in the second direction D2 gradually increases from the flat portion 31 to the large-diameter portion 33 in "ascending order of L12, L22, and L32". That means, when viewed from the Y-axis direction, the second core shaft 30 has a width gradually increasing from the large-diameter portion 33 on the proximal end side to the flat portion 31 on the distal end side (FIG. 6). Incidentally, regarding the flat portion 31, the intermediate portion 32, and the large-diameter portion 33, concrete values of each length L11, L12, L21, L22, L31, and L32, and a concrete value of the length in the axis line O (X axis) direction can be arbitrarily determined.

Incidentally, in the embodiment in FIG. 2, the large-diameter portion 33 of the second core shaft 30 is joined to the first core shaft 10 such that a position of the proximal end portion of the large-diameter portion 33 and a position of the proximal end portion of the small-diameter portion 11 coincide with each other in the axis line O (X axis) direction. However, the position of the proximal end portion of the large-diameter portion 33 and the position of the proximal end portion of the small-diameter portion 11 in the axis line O direction may be inconsistent with each other. For example, the proximal end portion of the large-diameter portion 33 may be positioned on the −X axis direction side of the proximal end portion of the small-diameter portion 11.

Figure 7:
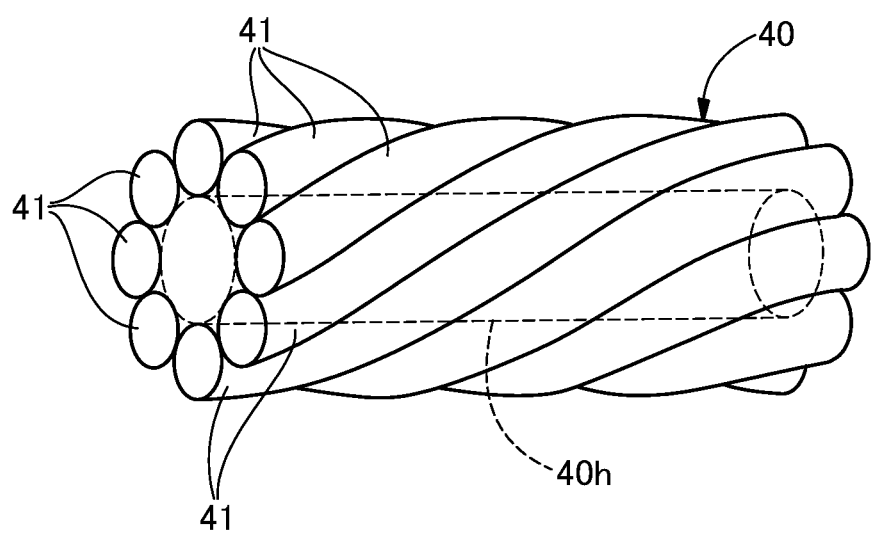
FIG. 7 is a perspective view illustrating a schematic configuration of a covering portion.

FIG. 7 is a perspective view illustrating a schematic configuration of the covering portion 40. The covering portion 40 according to the first embodiment is a multi-thread coil obtained by winding eight wires 41, and is less susceptible to plastic deformation than the second core shaft 30 and more susceptible to plastic deformation than the first core shaft 10. The covering portion 40 can be formed e.g. in such a way that the eight wires 41 are tightly twisted around a cored bar so as to be in contact with each other, then a residual stress is removed using a known heat treatment method, and the cored bar is drawn out. The covering portion 40 formed in this way is a multi-thread coil having an inner cavity 40h (dashed line) as illustrated. A material of the wire 41 may be the same as or different from that of the wire 21.

Incidentally, although any aspect can be adopted for the covering portion 40, the covering portion 40 is preferably configured to be less susceptible to plastic deformation than the second core shaft 30 and more susceptible to plastic deformation than the first core shaft 10, as described above. For example, a number of the wires constituting the covering portion 40 is not limited to eight, and can be arbitrarily determined. The covering portion 40 is not limited to the multi-thread coil, and may be a single-thread coil formed of one wire, or a tubular member made of a resin or a metal and formed into a tube shape, or alternatively may be coated with a hydrophobic resin material, a hydrophilic resin material, or a mixture thereof.

As illustrated in FIG. 2 to FIG. 5, inside the coil body 20, the covering portion 40 is arranged so as to cover a part of the distal end side of the first core shaft 10, the joint part JP, and the second core shaft 30. In other words, the first core shaft 10 and second core shaft 30 joined to each other pass through the inner cavity 40h of the covering portion 40 and extend in the axis line O direction. The distal end portion of the covering portion 40 is fixed by the distal end-side fixation portion 51 described later. The proximal end portion of the covering portion 40 is disposed in the vicinity of the center of the first decreasing-diameter portion 12 of the first core shaft 10 (FIG. 2). Incidentally, the proximal end portion of the covering portion 40 may or may not be fixed to the first decreasing-diameter portion 12 of the first core shaft 10 using any joining agent.

The distal end-side fixation portion 51 is disposed on the distal end portion of the guide wire 1 and integrally holds the distal end portion of the flat portion 31 of the second core shaft 30, the distal end portion of the coil body 20, and the distal end portion of the covering portion 40. The distal end-side fixation portion 51 can be formed from any joining agent, e.g. a metal solder such as silver solder, gold solder, zinc, Sn—Ag alloy, and Au—Sn alloy, or an adhesive such as epoxy adhesive. The proximal end-side fixation portion 52 is disposed on the proximal end portion of the first large-diameter portion 15 of the first core shaft 10 and integrally holds the first core shaft 10 and the proximal end portion of the coil body 20. The proximal end-side fixation portion 52 can be formed from any joining agent in the same manner as for the distal end-side fixation portion 51. For the proximal end-side fixation portion 52 and the distal end-side fixation portion 51, the same joining agent or different joining agents may be used.

The intermediate fixation portion 61 integrally holds the coil body 20 and the first core shaft 10 in the vicinity of the intermediate portion of the coil body 20 in the axis line O direction. The intermediate fixation portion 61 can be formed from any joining agent in the same manner as for the distal end-side fixation portion 51. For the intermediate fixation portion 61 and the distal end-side fixation portion 51, the same joining agent or different joining agents may be used. Although one intermediate fixation portion 61 has been described as in the embodiment in FIG. 1, a plurality of intermediate fixation portions 61 may be disposed on the guide wire 1.

Herein, as illustrated in FIG. 2, a part where the joint part JP between the first core shaft 10 and the second core shaft 30 is covered by the covering portion 40 is referred to as "second region R2", a part where the second core shaft 30 (flat portion 31, intermediate portion 32, and large-diameter portion 33) on the distal end side of the joint part JP is covered by the covering portion 40 is referred to as "first region R1", a part where the first core shaft 10 (first decreasing-diameter portion 12) on the proximal end side of the joint part JP is covered by the covering portion 40 is referred to as "third region R3", and a part where the first core shaft 10 is exposed from the covering portion 40 is referred to as "fourth region R4". That means, in the first embodiment, the first region R1, the second region R2, the third region R3, and the fourth region R4 are disposed in this order from the distal end side to the proximal end side of the guide wire 1. In other words, the first region R1 is positioned on the most distal side, the second region R2 is positioned on the proximal end side of the first region R1, the third region R3 is positioned on the proximal end side of the second region R2, and the fourth region R4 is positioned on the proximal end side of the third region R3 (most proximal end side).

As described above, the first core shaft 10 is made of a superelastic material, and the second core shaft 30 is made of a material more susceptible to plastic deformation than of the first core shaft 10. The covering portion 40 is configured to be less susceptible to plastic deformation than the second core shaft 30 and more susceptible to plastic deformation than the first core shaft 10. Thus, a relationship of each member on the susceptibility to plastic deformation is expressed as "the second core shaft 30>the covering portion 40>the first core shaft 10". In addition, as illustrated in FIG. 1, the diameter of the first core shaft 10 (first decreasing-diameter portion 12) exposed from the covering portion 40 increases from the distal end side to the proximal end side, and becomes substantially the same as the outer diameter of the covering portion 40 in the vicinity of the boundary with the first large-diameter portion 15. As a result, the aforementioned susceptibility of each region in the guide wire 1 to plastic deformation gradually decreases from the first region R1 to the fourth region R4 in the order of (the first region R1>the second region R2>the third region R3>the fourth region R4).

As described above, in the first direction D1 according to the first embodiment, the second core shaft 30 made of a material more susceptible to plastic deformation than the first core shaft 10 is joined to the distal end side (–X axis direction) of the first core shaft 10 made of the super-elastic material. Thus, the distal end portion of the guide wire 1 can be easily shaped by squeezing the distal end portion of the guide wire 1 with e.g. fingertips or a tip of a syringe needle.

Additionally, in the guide wire 1 according to the first embodiment, the curvable directions of the guide wire 1 are conformed to each other between the joint part JP for the first and second core shafts 10 and 30 and the distal end side of the joint part JP, so that the shaped portion in the guide wire 1 can be prevented from being distorted. Specifically, as illustrated in the lower column of FIG. 3, in the joint part JP between the first and second core shafts 10 and 30, the guide wire 1 tends to curve in the second direction D2 perpendicular to the adjacent direction (first direction) between the first and second core shafts (in other words, the curve in the first direction D1 is restricted). In addition, the flat portion 31 and the intermediate portion 32 positioned on the distal end side of the joint part JP, the lengths L11 and L21 in the first direction D1 are longer than the lengths L12 and L22 respectively in the second direction D2 orthogonal to the first direction D1 (lower column of FIG. 5, lower column of FIG. 4). Thus, in the flat portion 31 and the intermediate portion 32, similarly to the joint part JP, the guide wire 1 tends to curve in the second direction D2 perpendicular to the adjacent direction (first direction D1) between the first and second core shafts 10 and 30 (in other words, the curve in the first direction D1 is restricted). In such a way, the curvable directions are conformed to each other, so that torsion between the joint part JP and the distal end side of the joint part JP can be prevented when the distal end side of the guide wire 1 is shaped, and therefore the guide wire 1 can be prevented from having a three-dimensional shape.

Furthermore, in the guide wire 1 according to the first embodiment, breakage of the second core shaft 30 accompanying the shaping can be prevented by conforming the length L31 in the first direction D1 and the length L32 in the second direction D2 to each other on the large-diameter portion 33 formed on the proximal end side of the second core shaft 30 (lower column of FIG. 3). Additionally, in the flat portion 31 formed on the distal end side of the second core shaft 30, torsion of the guide wire 1 accompanying the shaping can be prevented as described above (lower column of FIG. 5). Incidentally, the intermediate portion 32 of the second core shaft 30 may be omitted. Even in this case, torsion of the guide wire 1 accompanying the shaping can be prevented by the flat portion 31 where the length L11 in the first direction D1 is longer than the length L12 in the second direction D2.

Furthermore, in the guide wire 1 according to the first embodiment, the length L11 of the flat portion 31 of the second core shaft 30 in the first direction D1 is longer than the length L31 of the large-diameter portion 33 in the first direction D1, and the length L12 of the flat portion 31 in the second direction D2 is shorter than the length L32 of the large-diameter portion 33 in the second direction D2. Thus, the flat portion 31 and the intermediate portion 32 can be easily formed e.g. by pressing a distal end side of a cylindrical member or a quadrangular prism-shaped member in which the length in the first direction D1 and the length in the second direction D2 are substantially equal.

Furthermore, in the guide wire 1 according to the first embodiment, the first region R1 more susceptible to plastic deformation than the second region R2 adjacent to the proximal end side of the first region R1 is disposed on the distal end side of the guide wire 1 (FIG. 2). In addition, the covering portion 40 for covering the joint part JP between the first and second core shafts 10 and 30, and at least a part of the second core shaft 30 on the distal end side of the joint part JP is disposed on both the first region R1 and the second region R2 (FIG. 2: first region R1 and second region R2). Owing to this covering portion 40, the rigidity gap between the first and second core shafts 10 and 30 having different rigidities can be reduced, and therefore the joint part JP between the first and second core shafts 10 and 30 can be more easily shaped compared to a configuration without the covering portion 40. Furthermore, reduction in the rigidity gap between the first and second core shafts 10 and 30 in the covering portion 40 makes it possible to protect a part locally susceptible to deformation in the vicinity of the joint part JP, e.g. a part of the second core shaft on the distal end side of the joint part JP, a part of the first core shaft 10 on the proximal end side of the joint part JP (FIG. 2), or the like, to prevent breakage of the first and second core shafts 10 and 30, so that durability of the guide wire 1 can be improved.

Furthermore, in the guide wire 1 according to the first embodiment, the distal end portion of the covering portion 40 is fixed by the distal end-side fixation portion 51 for fixing the distal end portion of the flat portion 31 in the second core shaft 30 (FIG. 1 and FIG. 2). That means, in the guide wire 1 according to the first embodiment, the covering portion 40 is formed on the second core shaft 30 and also its distal end. In such a way, the second core shaft 30 made of a material susceptible to plastic deformation and also its distal end can be protected to prevent breakage of the second core shaft 30 accompanying shaping and use, so that durability of the guide wire 1 can be further improved.

Furthermore, in the guide wire 1 according to the first embodiment, the third region R3 less susceptible to plastic deformation than the second region R2 is disposed on the proximal end side of the second region R2 (FIG. 2: third region R3). Thereby, the first core shaft 10 positioned on the proximal end side of the joint part JP between the first and second core shafts 10 and 30 can be protected to prevent breakage of the first core shaft 10 accompanying shaping and use, so that durability of the guide wire 1 can be further improved. Furthermore, the fourth region R4 less susceptible to plastic deformation than the third region R3 is disposed on the proximal end side of the third region R3 (FIG. 2: the fourth region R4). Thereby, breakage of the first core shaft 10 can be further improved, so that durability of the guide wire 1 can be further improved. In addition, in the fourth region R4, the first core shaft 10 is exposed from the covering portion 40. Thus, a manufacturing cost of the guide wire 1 can be reduced e.g. compared to a configuration that the covering portion 40 is formed on the coil body 20 and also its proximal end portion.

Second Embodiment

Figure 8:
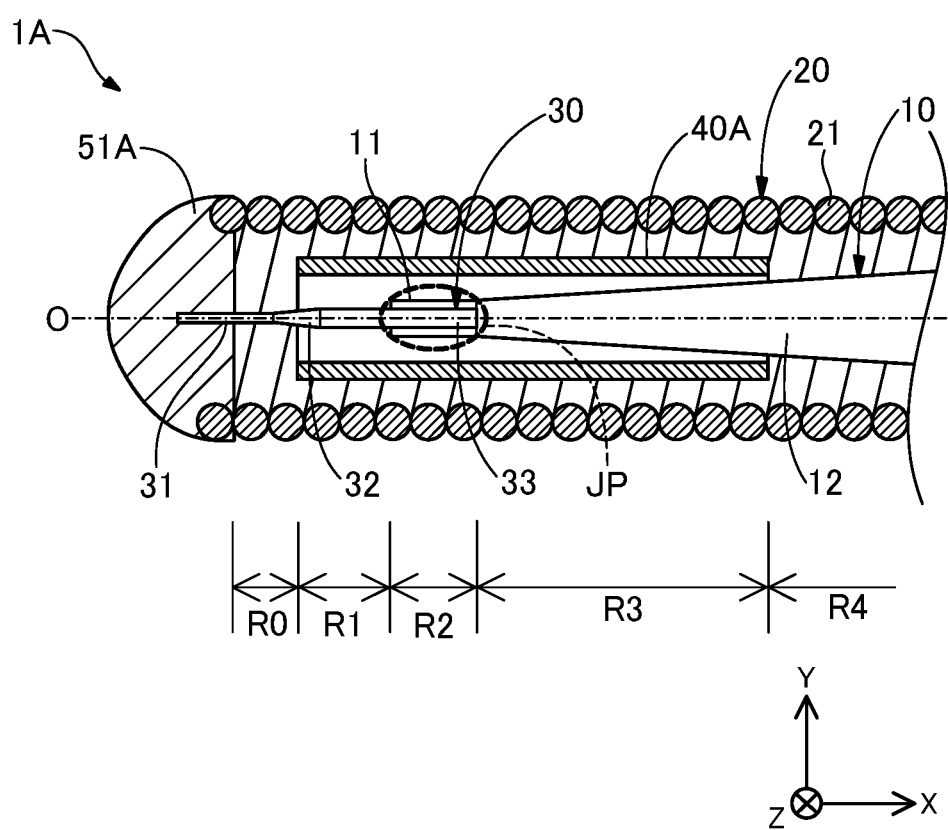
FIG. 8 is a partial sectional view illustrating a distal end side of a guide wire according to the second embodiment.

FIG. 8 is a partial sectional view illustrating a distal end side of a guide wire 1A according to the second embodiment. In the guide wire 1A according to the second embodiment, a distal end region R0 is disposed on the distal end side of the first region R1. In the distal end region R0, the second core shaft 30 (flat portion 31, intermediate portion 32, large-diameter portion 33) is not covered by a covering portion 40A but is exposed from the covering portion 40A. Specifically, the covering portion 40A according to the second embodiment has a length in the axis line O direction (X-axis direction) shorter than the length of the covering portion 40 according to the first embodiment, and is arranged so as to cover not the whole second core shaft 30 but a part on the proximal end side of the second core shaft 30. A proximal end portion of the covering portion 40A is fixed to the first decreasing-diameter portion 12 of the first core shaft 10 using any joining agent. A distal end portion of the covering portion 40A is not fixed to the distal end-side fixation portion 51A and opens in the embodiment of FIG. 8. Incidentally, the distal end portion of the covering portion 40A may be fixed to the second core shaft 30 using any joining agent.

In the second embodiment as described above, the distal end region R0, the first region R1, the second region R2, the third region R3, and the fourth region R4 are disposed in this order from the distal end side to the proximal end side of the guide wire 1A. As described above, a relationship of each member on the susceptibility to plastic deformation is expressed in "descending order of the second core shaft 30, the covering portion 40A, and the first core shaft 10". Thus, the distal end region R0 not covered by the covering portion 40A is more susceptible to plastic deformation than the first region R1 covered by the covering portion 40A. This means that the susceptibility of each region in the guide wire 1A to plastic deformation gradually decreases from the distal end region R0 to the fourth region R4 in "descending order of the distal end region R0, the first region R1, the second region R2, the third region R3, and the fourth region R4".

As described above, the same effect as in the aforementioned first embodiment can also be exhibited by the guide wire 1A according to the second embodiment. Furthermore, in the guide wire 1A according to the second embodiment, the distal end region R0 more susceptible to plastic deformation than the first region R1 is disposed on the distal end side of the first region. This makes it possible to further facilitate shaping of the distal end portion of the guide wire 1A. In addition, since the susceptibility of each region in the guide wire 1A to plastic deformation gradually increases from the fourth region R4 on the proximal end side to the distal end region R0 on the distal end side, it is possible to provide the guide wire 1A in which the distal end side is easily shaped while preventing breakage of the first and second core shafts 10 and 30 on the proximal end side.

Third Embodiment

Figure 9:
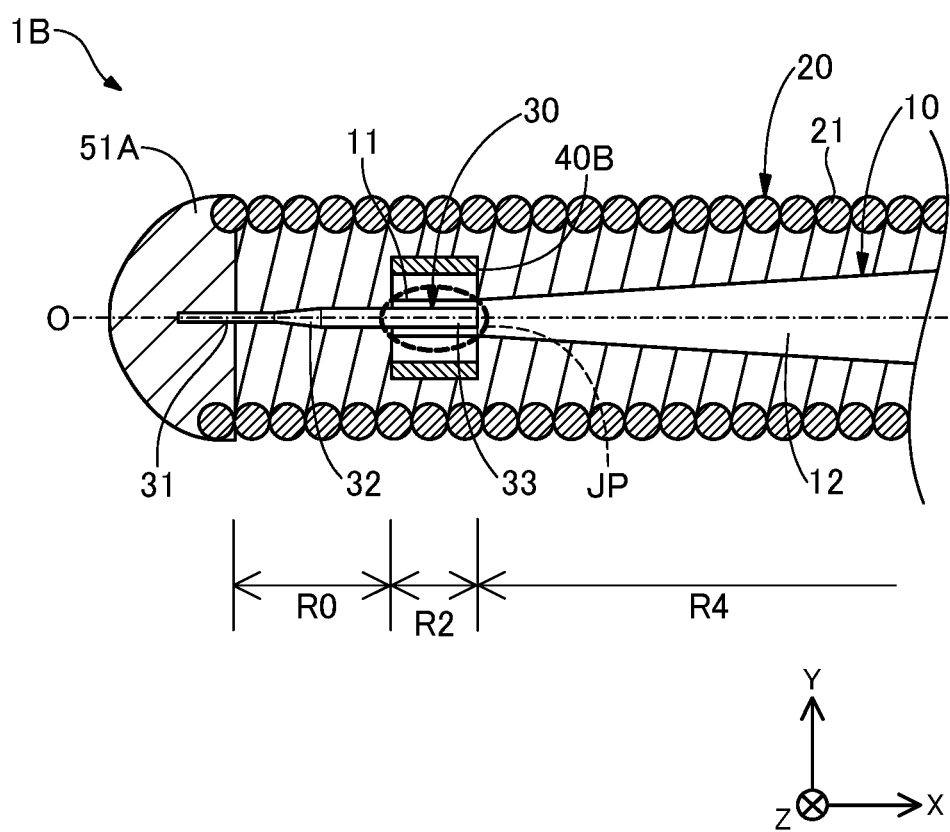
FIG. 9 is a partial sectional view illustrating a distal end side of a guide wire according to the third embodiment.

FIG. 9 is a partial sectional view illustrating a distal end side of a guide wire 1B according to the third embodiment. In the guide wire 1B according to the third embodiment, the first region R1 and the third region R3 in the configuration according to the second embodiment are not formed. Specifically, a covering portion 40B according to the third embodiment has a length in the axis line O direction (X-axis direction) shorter than that of the covering portion 40A according to the second embodiment and covers only the joint part JP between the first and second core shafts 10 and 30. In other words, the second core shaft 30 (flat portion 31, intermediate portion 32, large-diameter portion 33) positioned on the distal end side of the joint part JP is exposed from the covering portion 40B, and the first core shaft 10 (first decreasing-diameter portion 12) positioned on the proximal end side of the joint part JP is exposed from the covering portion 40B. Incidentally, at least one of a distal end portion and a proximal end portion of the covering portion 40B may be fixed to at least one of the small-diameter portion 11 of the first core shaft 10 and the large-diameter portion 33 of the second core shaft 30 using any joining agent.

In the third embodiment as described above, the distal end region R0, the second region R2, and the fourth region R4 are disposed in this order from the distal end side to the proximal end side of the guide wire 1B. The susceptibility of each region to plastic deformation gradually decreases from the distal end region R0 to the fourth region R4 in "descending order of the distal end region R0, the second region R2, and the fourth region R4". Thus, the same effect as in the second embodiment can also be exhibited by the guide wire 1B according to the third embodiment.

Fourth Embodiment

Figure 10:
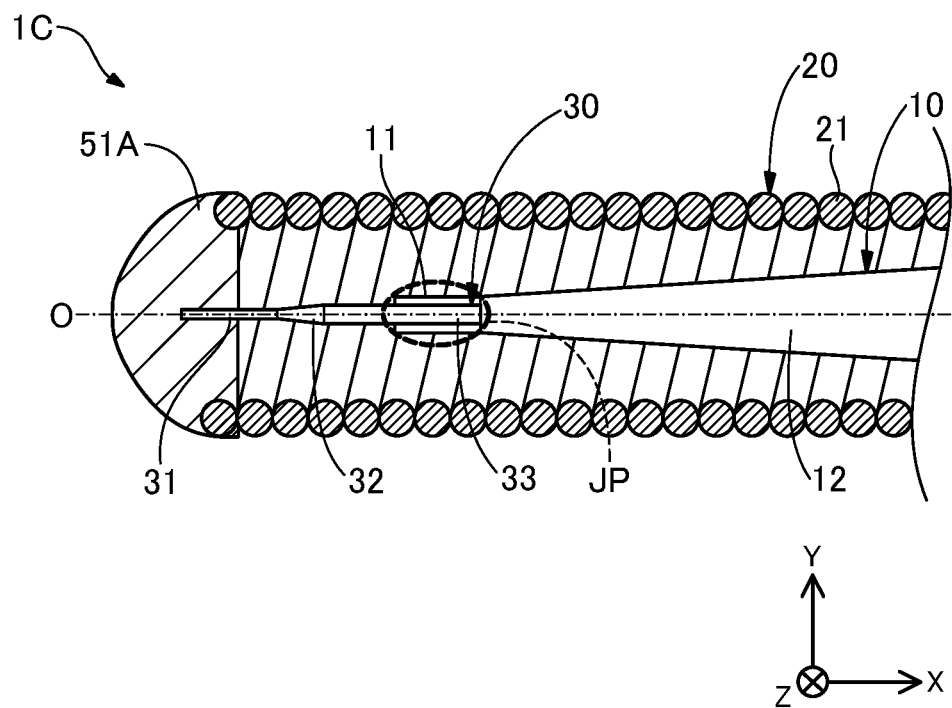
FIG. 10 is a partial sectional view illustrating a distal end side of a guide wire according to the fourth embodiment.

FIG. 10 is a partial sectional view illustrating a distal end side of a guide wire 1C according to the fourth embodiment. The guide wire 1C according to the fourth embodiment does not include the covering portion 40. Thus, the guide wire 1C does not have each of the aforementioned regions (distal end region R0, first to fourth regions R1 to R4). The same effect as in the first embodiment can also be exhibited by such a guide wire 1C according to the fourth embodiment. That means, a distal end portion of the guide wire 1C can be easily shaped, and when shaping the distal end side of the guide wire 1C, torsion between the joint part JP and the distal end side of the joint part JP can be prevented. In addition, the flat portion 31 of the second core shaft 30 can be easily formed.

Fifth Embodiment

Figure 11:
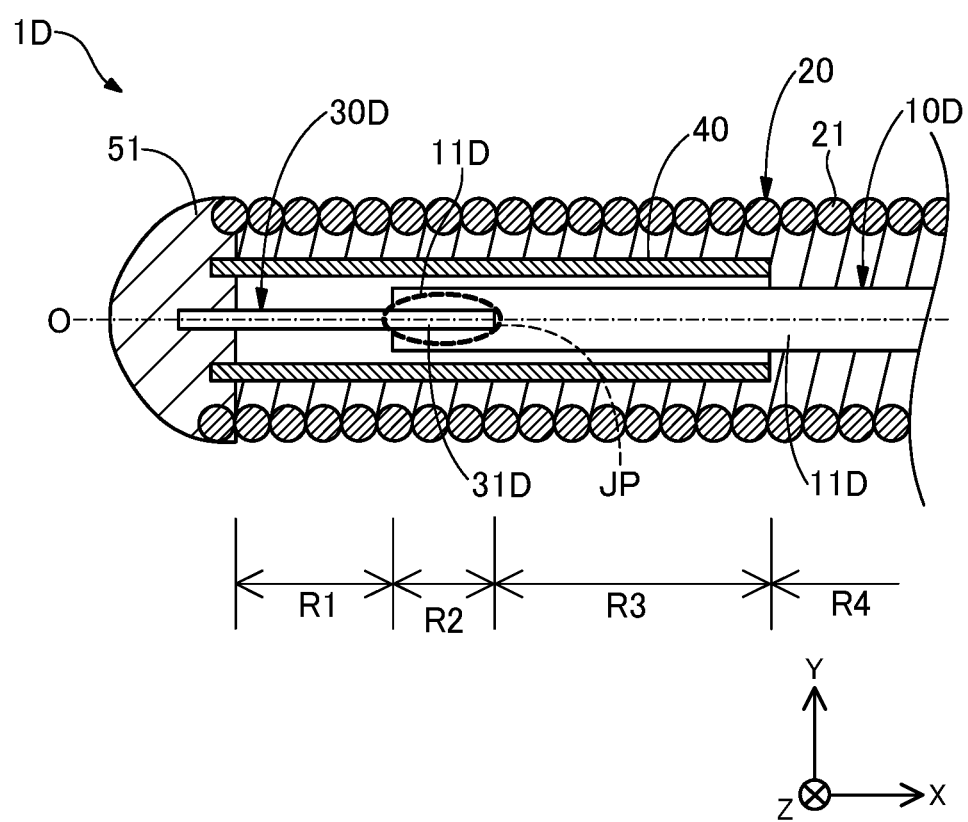
FIG. 11 is a partial sectional view illustrating a distal end side of a guide wire according to the fifth embodiment.

FIG. 11 is a partial sectional view illustrating a distal end side of a guide wire 1D according to the fifth embodiment. The guide wire 1D according to the fifth embodiment includes a first core shaft 10D instead of the first core shaft 10 and a second core shaft 30D instead of the second core shaft 30. On the distal end portion of the first core shaft 10D, a small-diameter portion 11D having a larger diameter and a longer length in the axis line O direction (X-axis direction) than those in the first embodiment is formed. On a distal end side of the small-diameter portion 11D, the joint part JP between the first and second core shafts 10 and 30 is disposed in the same manner as in the first embodiment. Incidentally, the first decreasing-diameter portion 12 may or may not be formed on the first core shaft 10D.

Figure 12:
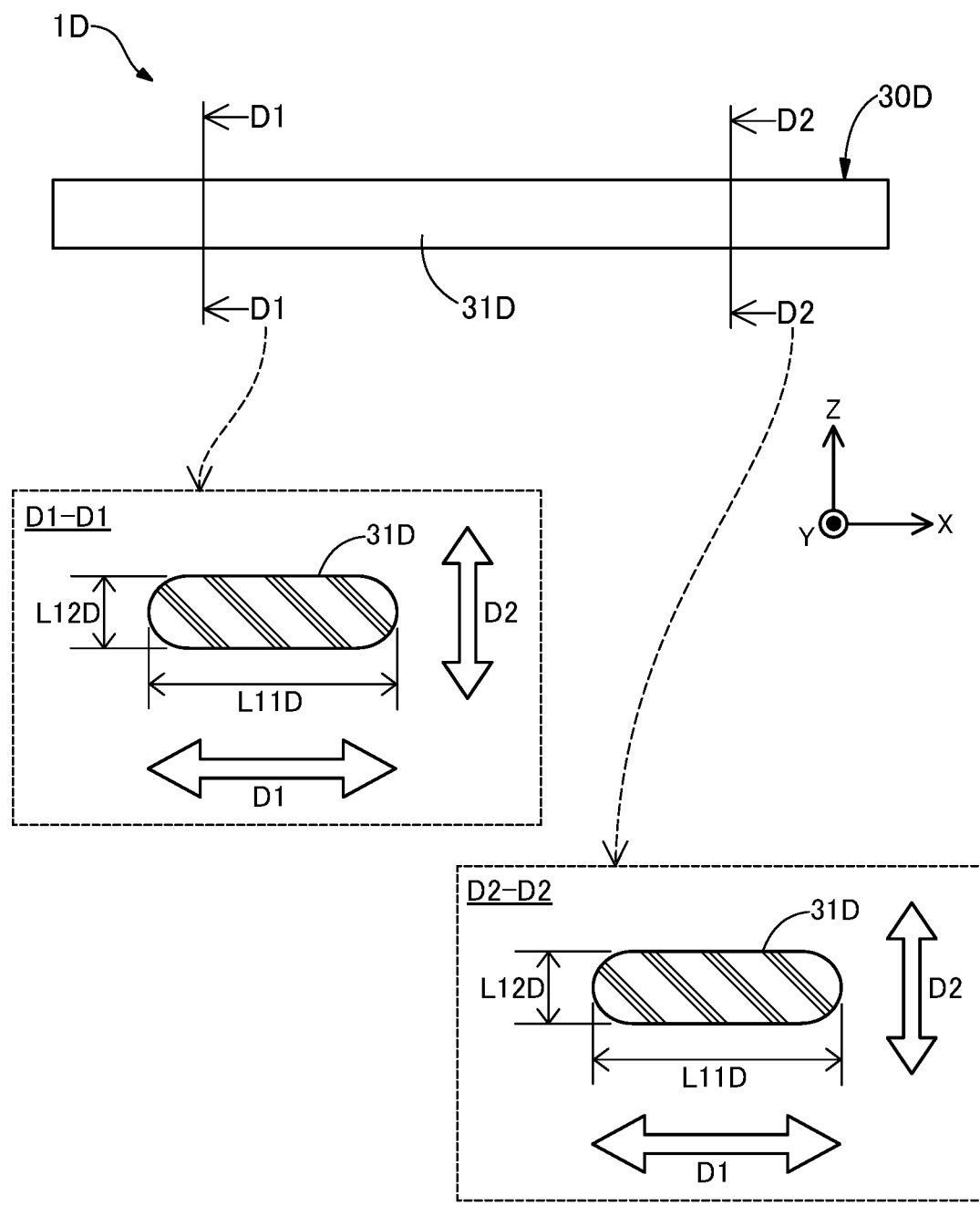
FIG. 12 is an explanatory diagram illustrating a second core shaft according to the fifth embodiment.

FIG. 12 is an explanatory diagram illustrating the second core shaft 30D according to the fifth embodiment. In FIG. 12, an appearance of the second core shaft 30D viewed in the Y-axis direction is illustrated in the upper column, and each sectional view taken along line D1-D1 and line D2-D2 is illustrated in the lower column. As illustrated in FIG. 12, the second core shaft 30D is composed of a flat portion 31D throughout the axis line O direction (X-axis direction), and does not have the aforementioned intermediate portion 32 and large-diameter portion 33. In the flat portion 31D, a length L11D in the first direction D1 is longer than a length L12D in the second direction D2 on both the D1-D1 cross section on the distal end side and the D2-D2 cross section on the proximal end side. This configuration is the same as of the flat portion 31 according to the first embodiment. The second core shaft 30D according to the fifth embodiment can be easily formed e.g. by pressing a whole of a cylindrical member or a quadrangular prism-shaped member in which the length in the first direction D1 and the length in the second direction D2 are substantially equal.

The same effect as in the first embodiment can also be exhibited by such a guide wire 1D according to the fifth embodiment. Incidentally, in the guide wire 1D according to the fifth embodiment, at least one of the first core shaft 10D and the second core shaft 30D may have the same configuration as in the first embodiment.

Sixth Embodiment

Figure 13:
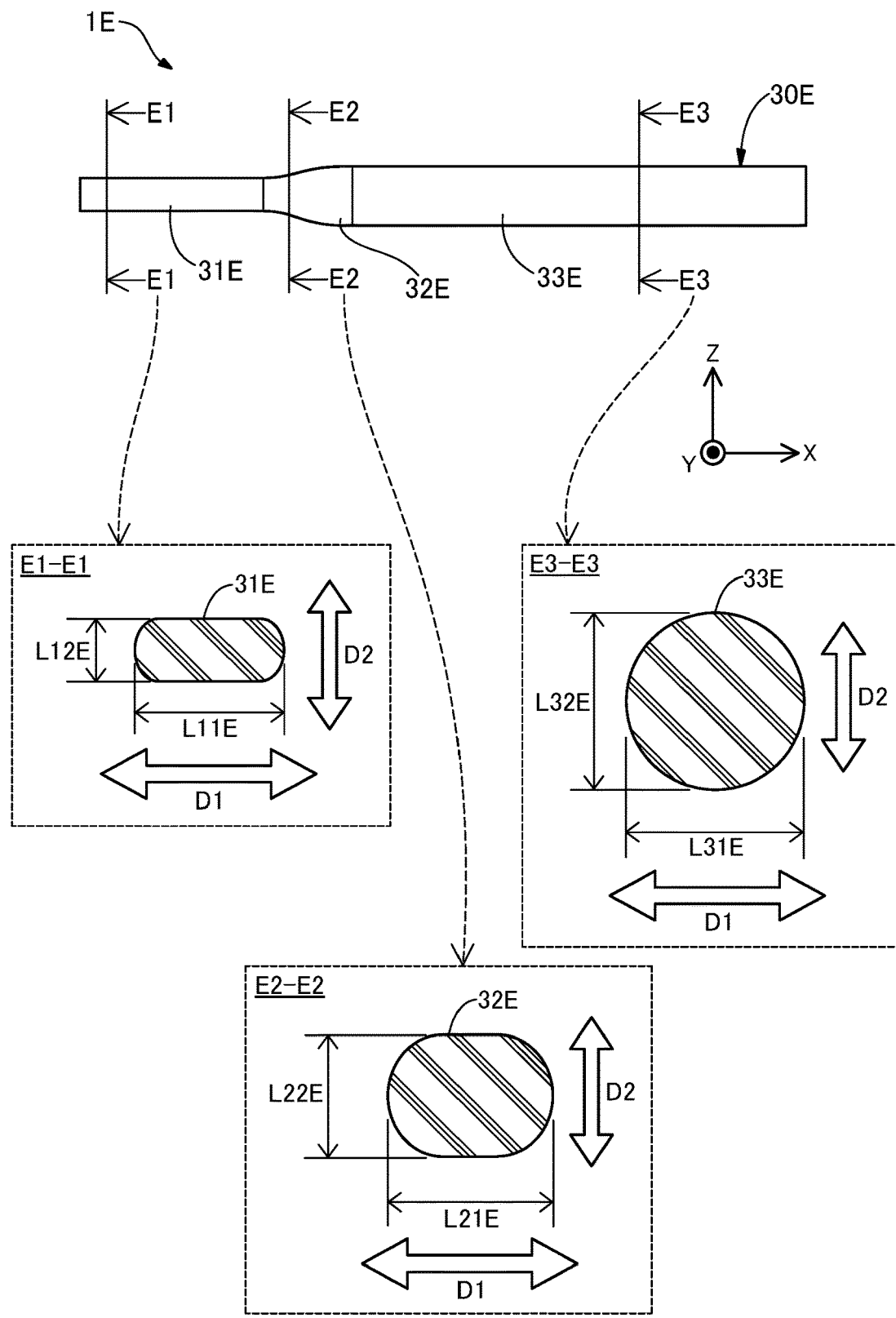
FIG. 13 is an explanatory diagram illustrating a second core shaft according to the sixth embodiment.

FIG. 13 is an explanatory diagram illustrating a second core shaft 30E according to the sixth embodiment. In FIG. 13, an appearance of the second core shaft 30E viewed from the Y-axis direction is illustrated in the upper column, and each sectional view taken along line E1-E1, line E2-E2, and line E3-E3 is illustrated in the lower column. A guide wire 1E according to the sixth embodiment includes the second core shaft 30E illustrated in FIG. 13 instead of the second core shaft 30. The second core shaft 30E has a width gradually decreasing from a large-diameter portion 33E positioned on the proximal end side to a flat portion 31E positioned on the distal end side.

As illustrated in the E1-E1 sectional view, the flat portion 31E has a substantially flat transverse sectional shape in which a length L11E in the first direction D1 is longer than a length L12E in the second direction D2. In addition, as illustrated in the E2-E2 sectional view, an intermediate portion 32E has a substantially elliptical transverse sectional shape in which a length L21E in the first direction D1 is longer than a length L22E in the second direction D2. As illustrated in the E3-E3 sectional view, the large-diameter portion 33E has a substantially circular transverse sectional shape in which a length L31E in the first direction D1 and a length L32E in the second direction D2 are substantially equal. These configurations are the same as of the flat portion 31, the intermediate portion 32, and the large-diameter portion 33 in the first embodiment.

On the other hand, the length of each portion in the first direction D1 in the second core shaft 30E gradually increases from the flat portion 31E to the large-diameter portion 33E in "ascending order of L11E, L21E, and L31E". This order is in converse relation with the order in the first embodiment. In addition, the length of each portion in the second direction D2 in the second core shaft 30E gradually increases from the flat portion 31E to the large-diameter portion 33E in "ascending order of L12E, L22E, and L32E", and this order is the same as in the first embodiment. The same effect as in the first embodiment can also be exhibited by the guide wire 1E according to the sixth embodiment, having such a second core shaft 30E.

Seventh Embodiment

Figure 14:
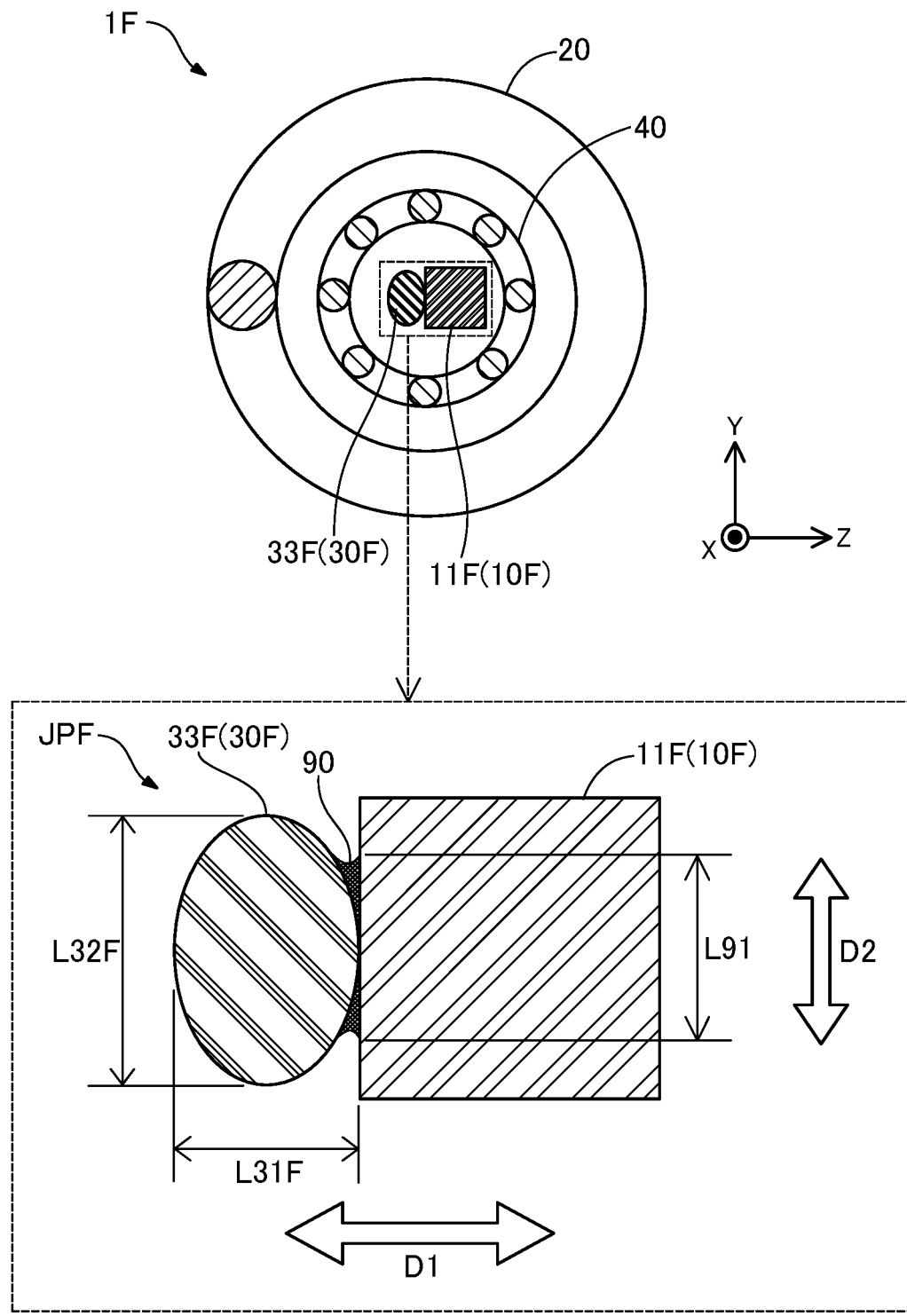
FIG. 14 is a sectional view illustrating a guide wire according to the seventh embodiment taken along line A-A (FIG. 2).

FIG. 14 is a sectional view illustrating a guide wire 1F according to the seventh embodiment taken along line A-A (FIG. 2). In FIG. 14, a sectional view taken along line A-A is illustrated in the upper column, and a partial enlarged view of the vicinity of a joint part JPF is illustrated in the lower column. In the guide wire 1F according to the seventh embodiment, a first core shaft 10F (small-diameter portion 11F) corresponding to the joint part JPF has a substantially rectangular transverse sectional shape, and a second core shaft 30F (large-diameter portion 33F) corresponding to the joint part JPF has a substantially elliptical transverse sectional shape having a major axis and a minor axis. The joint part JPF according to the seventh embodiment is formed by filling a gap between the small-diameter portion 11F and the large-diameter portion 33F adjacent to each other in the first direction D1 with the joining agent 90. For the joining agent 90, the metal solder or the adhesive described as examples in the first embodiment can be used. The joining agent 90 according to the seventh embodiment may be the same as or different from that in the first embodiment.

Incidentally, unlike the first embodiment, in the large-diameter portion 33F of the second core shaft 30F, a length L31F in the first direction D1 is shorter than a length L32F in the second direction D2. However, like the first embodiment, in a flat portion 31 of the second core shaft 30F, not illustrated in the figure, a length L11 in the first direction D1 is longer than a length L12 in the second direction D2.

The same effect as in the first embodiment can also be exhibited by such a guide wire 1F according to the seventh embodiment. Furthermore, in the guide wire 1F according to the seventh embodiment, on the joint part JPF, the first core shaft 10F (FIG. 14: small-diameter portion 11F) has a substantially rectangular transverse sectional shape, and the second core shaft 30F (FIG. 14: large-diameter portion 33F) has a substantially elliptical transverse sectional shape, and therefore the shapes of them are different. Thereby, as illustrated in FIG. 14, a contact face between the first and second core shafts 10F and 30F adjacent to each other on the joint part JPF increases compared to the first embodiment in which the small-diameter portion 11F and the large-diameter portion 33F have the same shape. In the guide wire 1F according to the seventh embodiment, a joining strength between the first and second core shafts 10F and 30F can be improved by filling this contact face as a joining face L91 with the joining agent 90.

Incidentally, the large-diameter portion 33F of the second core shaft 30F is joined to the small-diameter portion 11F of the first core shaft 10F such that a major axis is oriented in the Y-axis direction and a minor axis is oriented in the Z-axis direction. However, the arrangement of the large-diameter portion 33F may be reversed such that the minor axis is oriented in the Y-axis direction and the major axis is oriented in the Z-axis direction. In addition, shapes of parts (small-diameter portion 11F, large-diameter portion 33F) of the first and second core shafts 10F and 30F corresponding to the joint part JPF can exert the effect of the seventh embodiment as long as the shapes are different from each other, and any shape other than the substantially rectangular shape and the substantially elliptical shape described above can be adopted.

Eighth Embodiment

Figure 15:
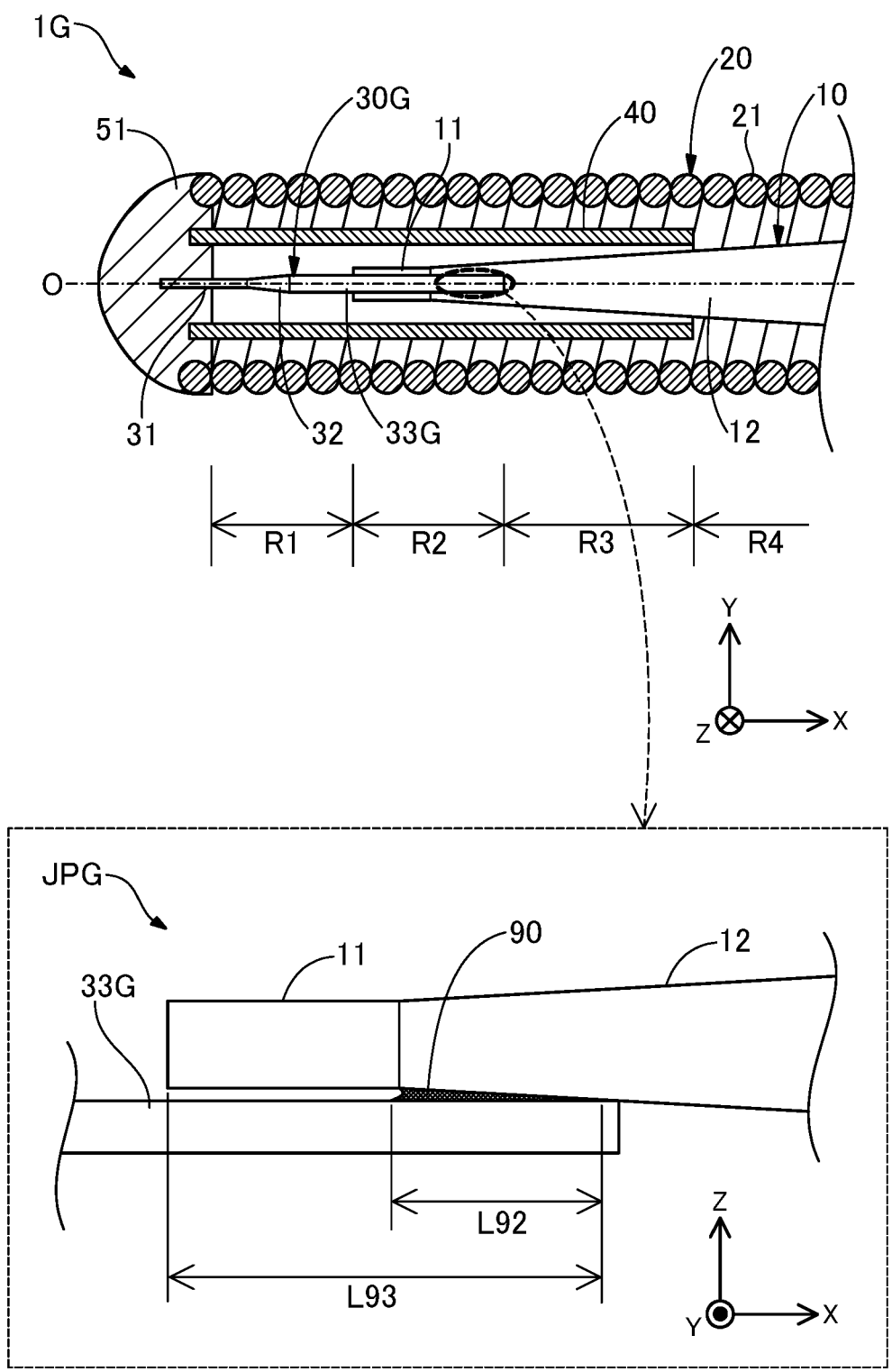
FIG. 15 is a partial sectional view illustrating a distal end side of a guide wire according to the eighth embodiment.

FIG. 15 is a partial sectional view illustrating a distal end side of a guide wire 1G according to the eighth embodiment. In FIG. 15, a partial sectional view of the distal end side of the guide wire 1G is illustrated in the upper column, and first and second core shafts 10 and 30G in the vicinity of a joint part JPG viewed from the Y-axis direction are illustrated in the lower column. In the guide wire 1G according to the eighth embodiment, the joint part JPG between the first and second core shafts 10 and 30G is disposed between the first decreasing-diameter portion 12 of the first core shaft 10 and the proximal end portion (large-diameter portion 33G) of the second core shaft 30G. The first decreasing-diameter portion 12 gradually decreases in the outer diameter from the proximal end side to the distal end side (lower column of FIG. 15), and has a substantially circular transverse sectional shape. As illustrated in the lower column of FIG. 15, the joint part JPG is formed by filling a gap between the first decreasing-diameter portion 12 and the large-diameter portion 33G adjacent to each other in the first direction D1 with the joining agent 90 and hardening the joining agent 90. For the joining agent 90, the metal solder or the adhesive described as examples in the first embodiment can be used. The joining agent 90 according to the eighth embodiment may be the same as or different from that in the first embodiment.

Incidentally, in the embodiment in the lower column of FIG. 15, the gap between the small-diameter portion 11 of the first core shaft 10 and the large-diameter portion 33G of the second core shaft 30G is a void without the joining agent 90. However, the void between the small-diameter portion 11 and the large-diameter portion 33G may be eliminated by filling this void with the joining agent 90 and hardening the joining agent 90. In the eighth embodiment, the joint part JPG includes a part where the small-diameter portion 11 and the large-diameter portion 33G are adjacent to each other, and the second region R2 includes a part where the small-diameter portion 11 and the large-diameter portion 33G are adjacent to each other (upper column of FIG. 15: second region R2).

The same effect as in the first embodiment can also be exhibited by such a guide wire 1G according to the eighth embodiment. Furthermore, in the guide wire 1G according to the eighth embodiment, the first decreasing-diameter portion 12 having a decreasing outer diameter is formed on the distal end side of the first core shaft 10, and the joint part JPG to which the second core shaft 30G (large-diameter portion 33G) is joined is disposed on this first decreasing-diameter portion 12. Thus, as illustrated in the lower column of FIG. 15, even if the first and second core shafts 10 and 30G on the joint part JPG have the same transverse sectional shape (FIG. 3), durability of the guide wire can be improved because the joint part JPG includes a joint on the large-diameter part of the first core shaft 10.

Ninth Embodiment

Figure 16:
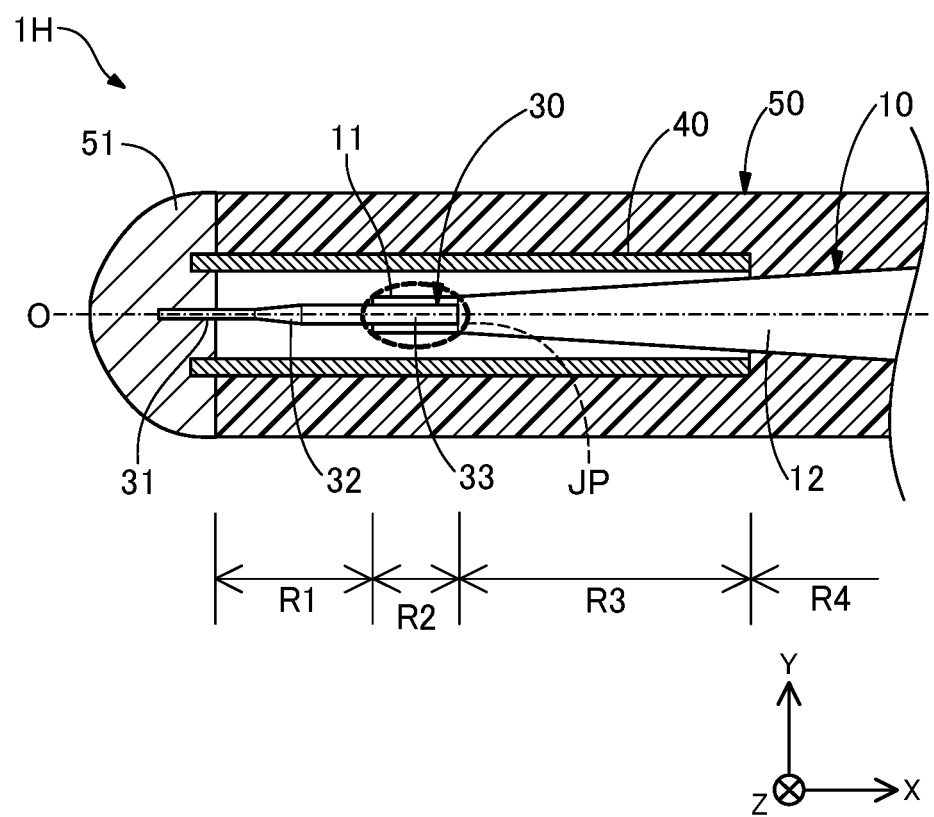
FIG. 16 is a partial sectional view illustrating a distal end side of a guide wire according to the ninth embodiment.

FIG. 16 is a partial sectional view illustrating a distal end side of a guide wire 1H according to the ninth embodiment. The guide wire 1H according to the ninth embodiment includes a resin body 50 instead of the coil body 20. The resin body 50 is arranged so as to cover the outside of the covering portion 40 and the first core shaft 10 not covered by the covering portion 40 (exposed from the covering portion 40). The same effect as in the first embodiment can also be exhibited by such a guide wire 1H according to the ninth embodiment.

Modification Examples of the Embodiments

Note that the disclosed embodiments are not limited to the above embodiments, and can be implemented in various aspects without departing from the gist of the disclosed embodiments. For example, the following modifications are also possible.

Modification Example 1

In the aforementioned first to tenth embodiments, the configurations of the guide wires 1, 1A to 1H, have been described as examples. However, the configuration of the guide wire can be variously changed. For example, the guide wire according to each embodiment has been explained as a medical appliance used for inserting a catheter into a blood vessel, but can be configured as a guide wire to be inserted into each organ in a human body, such as a lymphatic system, a biliary system, a urinary system, respiratory system, a digestive system, a secretory gland, and a genital organ. For example, the guide wire may be configured such that the second decreasing-diameter portion and the second large-diameter portion are absent, and the whole first core shaft is covered by the coil body. For example, the guide wire may be productized in a state that the distal end side is previously curved.

Modification Example 2

In the first to ninth embodiments, the configurations of the first and second core shafts 10, 10D, 10F, 30, 30D, 30E, 30F, and 30G have been described as examples. However, the configurations of the first and second core shafts can be variously modified. For example, the first core shaft may be configured so as not to have the first decreasing-diameter portion and the second decreasing-diameter portion and so as to have a constant diameter throughout the axis line O. For example, in the joint part JP (FIG. 3), the arrangements of the first and second core shafts in the first direction D1 (Z-axis direction) may be reversed. For example, the first core shaft may be composed of a plurality of core shaft members that are joined together. In this case, each core shaft member may be made of the same material or different materials.

Modification Example 3

In the first to ninth embodiments, the configuration of the coil body 20 has been described as an example. However, the configuration of the coil body can be variously changed. For example, the coil body may have a densely-wound structure without gaps between the wires adjacent to each other, or a coarsely-wound structure with gaps between the adjacent wires, or a mixed structure of the densely-wound structure and the coarsely-wound structure. In addition, the coil body may have a resin layer coated with e.g. a hydrophobic resin material, a hydrophilic resin material, or a mixture thereof. For example, a transverse sectional shape of the wire of the coil body is not necessarily the substantially circle.

Modification Example 4

The configurations of the guide wires 1, 1A to 1H according to the first to ninth embodiments and the configurations of the guide wires according to the modification examples 1 to 3 may be appropriately combined. For example, in the guide wire 1A according to the second embodiment (configured so as to include the distal end region R0), the guide wire 1B according to the third embodiment (configured so as not to include the first region R1 and the third region R3), and the guide wire 1C according to the fourth embodiment (configured so as not to include the covering portion), the second core shaft 30D described in the fifth embodiment and 30E described in the sixth embodiment may be used. Similarly, for example, in the guide wires 1A to 1C according to the second to fourth embodiments, the transverse sectional shapes of the first and second core shafts may be the shape described in the seventh embodiment. For example, in the guide wires 1A to 1C according to the second to fourth embodiments, the configuration of the joint part JP described in the seventh embodiment (configuration in which the joint part JP is disposed on the first decreasing-diameter portion of the first core shaft) may be adopted.

As described above, the present aspects have been explained based on the embodiments and the modification examples, and the embodiments of the aforementioned aspects are intended to facilitate understanding of the present aspects and not to limit the present aspects. The present aspects can be modified and improved without departing from the gist of the aspects and claims, and the present aspects include equivalents thereof. In addition, if technical characteristics of the present aspects are not explained as essentials in this specification, the technical characteristics can be appropriately deleted.

DESCRIPTION OF REFERENCE NUMERALS 1, 1A to 1H. Guide wire
10, 10D, 10F. First core shaft
11, 11D, 11F. Small-diameter portion
12. First decreasing-diameter portion
15. First large-diameter portion
16. Second decreasing-diameter portion
17. Second large-diameter portion
20. Coil body
21. Wire
30, 30D, 30E, 30F, 30G. Second core shaft
31, 31D, 31E. Flat portion
32, 32E. Intermediate portion
33, 33E, 33F, 33G. Large-diameter portion
40, 40A, 40B. Covering portion
40h. Inner cavity
41. Wire
50. Resin body
51, 51A. Distal end-side fixation portion
52. Proximal end-side fixation portion
61. Intermediate fixation portion
90. Joining agent

What is claimed is:

1. A guide wire comprising:
    a solid first core shaft including a superelastic material;
    a solid second core shaft (i) including a material having higher plastic deformability than that of the first core shaft, and (ii) being joined to a distal end side of the first core shaft on a proximal end side of the second core shaft;
    a flat portion formed on a distal end portion of the second core shaft; and
    a joint part disposed between the first core shaft and the second core shaft, wherein
    the first core shaft is adjacent to the second core shaft in a first direction at the joint part, the first core shaft and the second core shaft overlapping at the joint part,
    the flat portion has a length in the first direction in a transverse section that is longer than a length in a second direction orthogonal to the first direction,
    a distal end of the first core shaft extends further distal than a proximal end of the second core shaft, and
    at the joint part, the first core shaft and the second core shaft overlap when viewed in the first direction and do not overlap when viewed in the second direction.

2. The guide wire according to claim 1, wherein the second core shaft further comprises:
    a large-diameter portion where a length in the first direction and a length in the second direction are substantially equal in the transverse section; and
    an intermediate portion disposed between the large-diameter portion and the flat portion,
    wherein the joint part is disposed on the large-diameter portion.

3. The guide wire according to claim 2, wherein the length in the first direction of the flat portion is longer than the length in the first direction of the large-diameter portion, and
    the length in the second direction of the flat portion is shorter than the length in the second direction of the large-diameter portion.

4. The guide wire according to claim 1, further comprising:
    a covering portion for covering the joint part between the first core shaft and the second core shaft, and at least a part on the distal end side of the joint part in the second core shaft,
    wherein, from a distal end side to the proximal end side of the guide wire, (i) a first region where the second core shaft on the distal end side of the joint part is covered by the covering portion, and (ii) a second region adjacent to the first region where the joint part is covered by the covering portion, are disposed, and
    the first region has higher plastic deformability than the second region.

5. The guide wire according to claim 1, wherein a transverse sectional shape of the first core shaft on the joint part is different from a transverse sectional shape of the second core shaft on the joint part.

6. The guide wire according to claim 1, wherein a decreasing-diameter portion is formed on the distal end side of the first core shaft, the decreasing-diameter portion having an outer diameter that decreases from the proximal end side to the distal end side, and
    the joint part is disposed on the decreasing-diameter portion.

7. The guide wire according to claim 2, further comprising:
    a covering portion for covering the joint part between the first core shaft and the second core shaft, and at least a part on the distal end side of the joint part in the second core shaft,
    wherein, from a distal end side to the proximal end side of the guide wire, (i) a first region where the second core shaft on the distal end side of the joint part is covered by the covering portion, and (ii) a second region adjacent to the first region where the joint part is covered by the covering portion, are disposed, and the first region has higher plastic deformability than the second region.

8. The guide wire according to claim 2, wherein a transverse sectional shape of the first core shaft on the joint part is different from a transverse sectional shape of the second core shaft on the joint part.

9. The guide wire according to claim 2, wherein a decreasing-diameter portion is formed on the distal end side of the first core shaft, the decreasing-diameter portion having an outer diameter that decreases from the proximal end side to the distal end side, and the joint part is disposed on the decreasing-diameter portion.

10. The guide wire according to claim 3, further comprising:

a covering portion for covering the joint part between the first core shaft and the second core shaft, and at least a part on the distal end side of the joint part in the second core shaft, wherein, from a distal end side to the proximal end side of the guide wire, (i) a first region where the second core shaft on the distal end side of the joint part is covered by the covering portion, and (ii) a second region adjacent to the first region where the joint part is covered by the covering portion, are disposed, and the first region has higher plastic deformability than the second region.

11. The guide wire according to claim 3, wherein a transverse sectional shape of the first core shaft on the joint part is different from a transverse sectional shape of the second core shaft on the joint part.

12. The guide wire according to claim 3, wherein a decreasing-diameter portion is formed on the distal end side of the first core shaft, the decreasing-diameter portion having an outer diameter that decreases from the proximal end side to the distal end side, and the joint part is disposed on the decreasing-diameter portion.

13. The guide wire according to claim 4, wherein a transverse sectional shape of the first core shaft on the joint part is different from a transverse sectional shape of the second core shaft on the joint part.

14. The guide wire according to claim 4, wherein a decreasing-diameter portion is formed on the distal end side of the first core shaft, the decreasing-diameter portion having an outer diameter that decreases from the proximal end side to the distal end side, and the joint part is disposed on the decreasing-diameter portion.

15. The guide wire according to claim 5, wherein a decreasing-diameter portion is formed on the distal end side of the first core shaft, the decreasing-diameter portion having an outer diameter that decreases from the proximal end side to the distal end side, and the joint part is disposed on the decreasing-diameter portion.

* * * * *